(12) United States Patent
Nelson

(10) Patent No.: US 11,098,813 B2
(45) Date of Patent: Aug. 24, 2021

(54) BINARY FLUID CONTROL VALVE SYSTEM

(71) Applicant: Allurion Technologies, Inc., Natick, MA (US)

(72) Inventor: David W. Nelson, Wayland, MA (US)

(73) Assignee: Allurion Technologies, Inc., Natick, MA (US)

( * ) Notice: Subject to any disclaimer, the term of this patent is extended or adjusted under 35 U.S.C. 154(b) by 0 days.

(21) Appl. No.: 16/505,468

(22) Filed: Jul. 8, 2019

(65) Prior Publication Data
US 2020/0011442 A1 Jan. 9, 2020

Related U.S. Application Data

(60) Provisional application No. 62/694,813, filed on Jul. 6, 2018.

(51) Int. Cl.
| | |
|---|---|
| *F16K 17/40* | (2006.01) |
| *A61F 5/00* | (2006.01) |
| *F16K 17/36* | (2006.01) |
| *F16K 17/38* | (2006.01) |
| *F16K 31/126* | (2006.01) |
| *F16K 31/00* | (2006.01) |

(52) U.S. Cl.
CPC .............. *F16K 17/40* (2013.01); *A61F 5/003* (2013.01); *F16K 17/36* (2013.01); *F16K 17/38* (2013.01); *F16K 31/002* (2013.01); *F16K 31/1264* (2013.01)

(58) Field of Classification Search
CPC .......... F16K 17/40; F16K 17/36; F16K 17/38; F16K 31/002; F16K 31/1264; A61F 5/003
USPC ..... 137/68.11, 72, 118.03, 468, 517, 540.11, 137/882, 79
See application file for complete search history.

(56) References Cited

U.S. PATENT DOCUMENTS

| | | | |
|---|---|---|---|
| 2,911,988 A | 11/1959 | Ravn | |
| 3,586,018 A | 6/1971 | Bogardh et al. | |
| 3,638,733 A * | 2/1972 | De Rouville | A62C 99/009 169/19 |
| 3,853,116 A | 12/1974 | Bucalo | |
| 4,133,315 A | 1/1979 | Berman et al. | |
| 4,141,771 A | 2/1979 | Barker et al. | |
| 4,370,374 A | 1/1983 | Raabe et al. | |
| 4,723,547 A | 2/1988 | Kullas et al. | |

(Continued)

FOREIGN PATENT DOCUMENTS

| | | |
|---|---|---|
| CA | 2925648 | 5/2007 |
| CA | 2865056 | 8/2013 |

(Continued)

OTHER PUBLICATIONS

Stony Brook Medicine "Obalon Swallowable Balloon Capsules" Feb. 21, 2017, 2 pages. Retrieved from the Internet [Sep. 2, 2020] URL: https://www.youtube.com/watch?v=CEznWcGacLI.

*Primary Examiner* — Minh Q Le
(74) *Attorney, Agent, or Firm* — Levine Bagade Han LLP

(57) ABSTRACT

Fluid control valves including single-opening, binary fluid control valves that are initially closed and can be opened one time only to allow a fluid transfer between two spaces separated by a fluid impermeable barrier. Applications of valves of this type include inflatable devices, including but not limited to medical device balloons, in particular gastric balloons for weight loss.

24 Claims, 13 Drawing Sheets

(56) References Cited

U.S. PATENT DOCUMENTS

| | | | |
|---|---|---|---|
| 4,732,188 A * | 3/1988 | Gabrlik | B60K 15/035 137/541 |
| 4,739,758 A | 4/1988 | Lai et al. | |
| 4,842,007 A | 6/1989 | Kurtz | |
| 4,899,747 A | 2/1990 | Garren et al. | |
| 4,949,756 A | 8/1990 | Melinyshyn et al. | |
| 5,018,665 A * | 5/1991 | Sulmone | F16K 31/002 236/93 A |
| 5,181,921 A | 1/1993 | Makita et al. | |
| 5,336,123 A | 8/1994 | Laske et al. | |
| 5,348,537 A | 9/1994 | Wiesner et al. | |
| 5,496,203 A | 3/1996 | Murray | |
| 5,507,808 A | 4/1996 | Becker | |
| 5,595,521 A | 1/1997 | Becker | |
| 5,950,624 A | 9/1999 | Hart | |
| 6,162,251 A | 12/2000 | Kredovski | |
| 6,259,953 B1 | 7/2001 | Lucchesi et al. | |
| 6,367,499 B1 * | 4/2002 | Taku | F16K 17/383 137/72 |
| 6,375,972 B1 | 4/2002 | Guo et al. | |
| 6,460,541 B1 | 10/2002 | Shah et al. | |
| 6,644,336 B2 | 11/2003 | Dolan | |
| 6,712,832 B2 | 3/2004 | Shah | |
| 6,814,097 B2 * | 11/2004 | Girouard | F16K 17/04 137/72 |
| 6,939,292 B2 | 9/2005 | Mizuno et al. | |
| 7,172,613 B2 | 2/2007 | Wazne | |
| 7,485,093 B2 | 2/2009 | Glukhovsky | |
| 7,854,745 B2 | 12/2010 | Brister et al. | |
| 8,183,227 B1 | 5/2012 | Perrin et al. | |
| 8,202,291 B1 | 6/2012 | Brister et al. | |
| 8,287,562 B2 | 10/2012 | Kasic, II | |
| 8,292,911 B2 | 10/2012 | Brister et al. | |
| 8,585,676 B2 | 11/2013 | Shah | |
| 8,740,845 B2 | 6/2014 | Shah et al. | |
| 8,784,486 B2 | 7/2014 | Schuessler | |
| 8,814,898 B2 | 8/2014 | Gaur et al. | |
| 8,870,907 B2 | 10/2014 | Gaur et al. | |
| 8,974,483 B2 | 3/2015 | Gaur et al. | |
| 9,387,107 B2 | 7/2016 | Gaur et al. | |
| 9,463,106 B2 | 10/2016 | Khieu et al. | |
| 9,662,239 B2 | 5/2017 | Brister et al. | |
| 9,827,128 B2 | 11/2017 | Brister et al. | |
| 9,827,129 B2 | 11/2017 | Gaur et al. | |
| 9,849,018 B2 | 12/2017 | Wecker et al. | |
| 10,182,932 B2 | 1/2019 | Moss et al. | |
| 10,307,279 B2 | 6/2019 | Wecker et al. | |
| 10,470,908 B2 | 11/2019 | Nelson et al. | |
| 10,583,024 B2 | 3/2020 | Nelson et al. | |
| 10,588,768 B2 | 3/2020 | Nelson et al. | |
| 2002/0183777 A1 | 12/2002 | Shannon | |
| 2002/0198470 A1 | 12/2002 | Imran et al. | |
| 2003/0106583 A1 * | 6/2003 | Weng | F16K 17/383 137/72 |
| 2003/0229263 A1 | 12/2003 | Connors et al. | |
| 2003/0229384 A1 | 12/2003 | Mon | |
| 2004/0101540 A1 | 5/2004 | Cooker | |
| 2004/0146559 A1 | 7/2004 | Sowden et al. | |
| 2004/0186502 A1 | 9/2004 | Sampson et al. | |
| 2005/0055039 A1 | 3/2005 | Burnett et al. | |
| 2005/0150548 A1 * | 7/2005 | Kita | F16K 17/383 137/72 |
| 2006/0222705 A1 | 10/2006 | Flanner et al. | |
| 2007/0010791 A1 | 1/2007 | Drechsler et al. | |
| 2007/0078476 A1 | 4/2007 | Hull, Sr. et al. | |
| 2008/0195226 A1 | 8/2008 | Williams et al. | |
| 2008/0241094 A1 | 10/2008 | Burnett et al. | |
| 2008/0243071 A1 | 10/2008 | Quijano et al. | |
| 2008/0249635 A1 | 10/2008 | Weitzner et al. | |
| 2008/0269555 A1 | 10/2008 | Paganon et al. | |
| 2008/0276992 A1 * | 11/2008 | Nomichi | F16K 17/383 137/79 |
| 2009/0024227 A1 | 1/2009 | Lesh | |
| 2009/0048684 A1 | 2/2009 | Lesh | |
| 2009/0118756 A1 | 5/2009 | Valencon | |
| 2009/0192535 A1 | 7/2009 | Kasic | |
| 2009/0259246 A1 | 10/2009 | Eskaros et al. | |
| 2009/0277515 A1 * | 11/2009 | Pechtold | F16K 31/003 137/468 |
| 2009/0299327 A1 | 12/2009 | Tilson et al. | |
| 2010/0062057 A1 | 3/2010 | Berge et al. | |
| 2010/0100116 A1 | 4/2010 | Brister et al. | |
| 2010/0114311 A1 | 5/2010 | Becker | |
| 2010/0121224 A1 | 5/2010 | Toyota et al. | |
| 2010/0137897 A1 | 6/2010 | Brister et al. | |
| 2010/0174307 A1 | 7/2010 | Birk | |
| 2010/0193050 A1 * | 8/2010 | Job | F16K 17/38 137/468 |
| 2010/0246165 A1 | 9/2010 | Diaz et al. | |
| 2010/0274194 A1 | 10/2010 | Sobelman et al. | |
| 2011/0004236 A1 | 1/2011 | Priplata et al. | |
| 2011/0112383 A1 | 5/2011 | Voss et al. | |
| 2012/0141544 A1 | 6/2012 | Fuisz et al. | |
| 2012/0141545 A1 | 6/2012 | Fuisz et al. | |
| 2012/0232576 A1 | 9/2012 | Brister et al. | |
| 2012/0273050 A1 * | 11/2012 | Metzger | E03F 5/0411 137/2 |
| 2013/0035711 A1 | 2/2013 | Schwab et al. | |
| 2013/0165873 A1 | 6/2013 | Morriss et al. | |
| 2013/0190796 A1 | 7/2013 | Tilson et al. | |
| 2013/0218190 A1 | 8/2013 | Gaur et al. | |
| 2013/0267984 A1 | 10/2013 | Gaur et al. | |
| 2013/0289604 A1 | 10/2013 | Brister et al. | |
| 2013/0296751 A1 | 11/2013 | Martin et al. | |
| 2014/0066967 A1 | 3/2014 | Levy et al. | |
| 2014/0188151 A1 | 7/2014 | Gaur et al. | |
| 2014/0296903 A1 | 10/2014 | Gaur et al. | |
| 2015/0196408 A1 | 7/2015 | Moss et al. | |
| 2016/0010758 A1 * | 1/2016 | Nomichi | F16K 17/383 137/72 |
| 2016/0109029 A1 | 4/2016 | Dulin | |
| 2016/0278957 A1 | 9/2016 | Gaur et al. | |
| 2017/0211715 A1 | 7/2017 | Balmaceda et al. | |
| 2017/0312111 A1 | 11/2017 | Sharma et al. | |
| 2018/0042747 A1 | 2/2018 | Gaur et al. | |
| 2018/0071127 A1 | 3/2018 | Wecker et al. | |
| 2018/0311484 A1 | 11/2018 | Lake et al. | |
| 2018/0344498 A1 | 12/2018 | Moss et al. | |
| 2019/0262157 A1 | 8/2019 | Nelson et al. | |
| 2019/0388258 A1 | 12/2019 | Nelson et al. | |
| 2019/0388259 A1 | 12/2019 | Nelson et al. | |

FOREIGN PATENT DOCUMENTS

| | | |
|---|---|---|
| CN | 201977967 | 9/2011 |
| EP | 2817062 | 12/2014 |
| EP | 3117865 | 1/2017 |
| JP | 2008-513132 | 5/2008 |
| JP | 2008-515464 | 5/2008 |
| JP | 2010-523280 | 7/2010 |
| JP | 2011-517611 | 6/2011 |
| WO | WO 2000/012167 | 3/2000 |
| WO | WO 2006/020929 | 2/2006 |
| WO | WO 2009/059802 | 5/2009 |
| WO | WO 2009/059803 | 5/2009 |
| WO | WO 2011/106157 | 9/2011 |
| WO | WO 2013/126593 | 8/2013 |
| WO | WO 2014/074625 | 5/2014 |
| WO | WO 2015/066545 | 5/2015 |
| WO | WO 2016/145076 | 9/2016 |
| WO | WO 2017/136840 | 8/2017 |
| WO | WO 2018/142761 | 8/2018 |
| WO | WO 2019/165449 | 8/2019 |
| WO | WO 2020/010359 | 1/2020 |

* cited by examiner

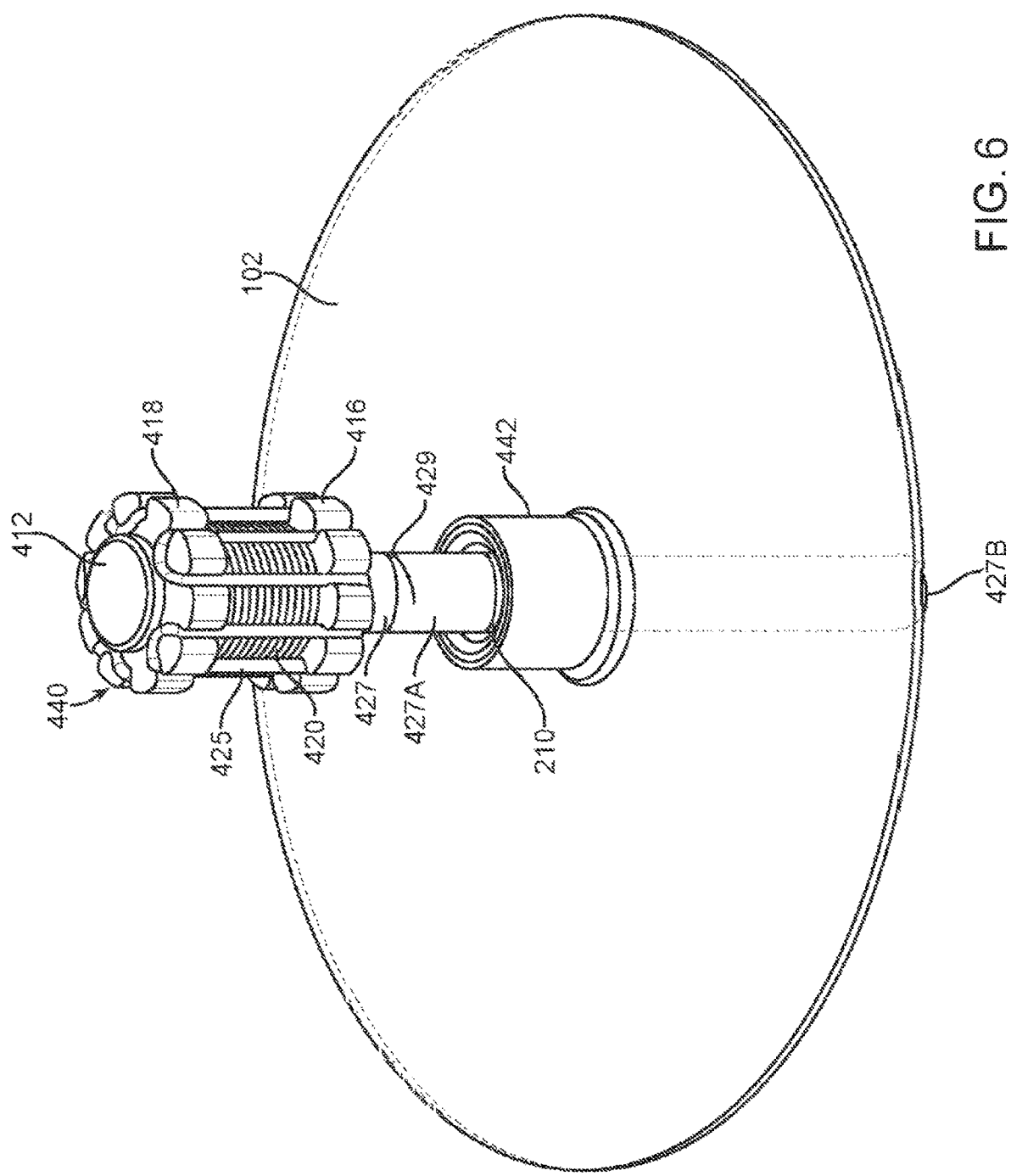

BINARY FLUID CONTROL VALVE SYSTEM

CROSS-REFERENCE TO RELATED APPLICATIONS

This application is a non-provisional of U.S. Provisional application No. 62/694,813 filed on Jul. 6, 2018, the entirety of which is incorporated by reference.

BACKGROUND OF THE INVENTION

The present invention generally relates to the field of fluid control valves and more particularly the field of single-opening, binary fluid control valves that are initially closed and can be opened one time only to allow a fluid transfer between two spaces separated by a fluid impermeable barrier. Areas of application for valves of this type include medical device balloons, in particular gastric balloons for weight loss.

According to 2010 World Health Organization data, 198 million Americans over the age of 15 are above target weight. Of these individuals, 89 million are considered overweight (25<Body Mass Index<30) and 109 million are considered obese (Body Mass Index>30). Worldwide, more than 1.4 billion adults age 20 and over are overweight, and 500 million are obese. Obesity places patients at increased risk of numerous, potentially disabling conditions including type 2 diabetes, heart disease, stroke, gallbladder disease, and musculoskeletal disorders. Compared with healthy weight adults, obese adults are more than three times as likely to have been diagnosed with diabetes or high blood pressure. In the United States it is estimated that one in five cancer-related deaths may be attributable to obesity in female non-smokers and one in seven among male non-smokers (>=50 years of age). On average, men and women who were obese at age 40 live 5.8 and 7.1 fewer years, respectively, than their healthy weight peers.

For the vast majority of the overweight and obese population for whom surgical obesity procedures are not appropriate, few efficacious and affordable interventions are currently available. Diet and exercise remain the front line approaches to obesity, however this approach has at best slowed the growth of the epidemic. To date, drug therapies have dose limiting side effects or have lacked meaningful long term efficacy.

One less-invasive intervention that has begun to gain popularity is an intragastric balloon. Intragastric balloons in their uninflated state can be placed endoscopically or positioned using other methods and, once in place, are typically filled with a filling fluid through a thin catheter or conduit extending up the esophagus from the device in the stomach to an external fluid supply. This catheter is then removed from the device and extracted from the body through the esophagus. Upon removal of the catheter, the catheter system must seal the fluid communication between the interior of the device and the gastric environment to maintain the balloon in its filled state for the proscribed time.

In some gastric balloons an endoscopic procedure is used to remove the balloon at the end of its proscribed time. Endoscopic procedures, while generally safe, inherently carry some risk to the patient, are invasive, require the patient to visit an endoscopy facility, and require the services and costs of an endoscopist. For these reasons various self-opening or non-invasively-triggered fluid release mechanisms or valves have been developed.

In particular, several self-opening release valves, as described in the following commonly assigned patents, publications, and provisional applications: U.S. Pat. No. 8,814,898 (ALLR-N-Z003.01-USS); U.S. Pat. No. 8,870,907 (ALLR-N-Z003.00-USX); U.S. Pat. No. 8,974,483 (ALLR-N-Z004.00-USS); U.S. Pat. No. 9,387,107 (ALLR-N-Z003.02-USS); U.S. Pat. No. 9,827,129 (ALLR-N-Z003.03-USS); U.S. Pat. No. 9,849,018 (ALLR-N-Z020.00-USS); U.S. 20150196408 (ALLR-N-Z004.01-USS); U.S. 20180042747 (ALLR-N-Z003.04-USS); U.S. 20180071127 (ALLR-N-Z020.01-USS); U.S. 20180168839 (ALLR-N-Z026.00-US); and Provisional Application Nos. 62/562,882, 62/635,272. The entirety of each of which is incorporated by reference herein. In addition, the valves described herein can be used with the devices described in the forgoing patents, publications and provisional applications.

However, in certain applications there may be a need for a device to rapidly deflate. Therefore, there remains a need for devices where a fluid release flow rate is increased to assist with fast deflation of the device. For instance, there also remains a need for a self-releasing valve that opens rapidly to its full open state.

SUMMARY OF THE INVENTION

The present invention relates to devices and methods for releasing a fluid from a reservoir. In particular, the invention relates to self-opening release valves for emptying balloon-like devices. More particularly the invention relates to self-opening valves that open rapidly after initiation of the opening process, where self-opening generally implies no direct human action. In some variations, the valves can achieve full aperture opening in a rapid manner.

The present disclosure includes fluid release mechanisms for use with fluid filled devices and are especially useful in gastric balloons for occupying a space within the patient's body. In one example such a medical device includes a fluid impermeable surface material forming a device body having an interior reservoir, the device body having a deployment profile and expandable to an active profile upon receiving the fluid filler material within the interior reservoir; a fluid path for evacuation of the fluid, a plug for sealing the fluid path, an energy storage element disposed to remove the plug from the fluid path, and a release material disposed to hold the plug in a sealing configuration in the evacuation path until the strength of the release material degrades below that which is needed to resist the energy storage element.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments and variations without departing from the scope of the invention.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention. Of the drawings:

FIG. 6 illustrates a perspective view of the fluid control valve as a plug is being inserted into a socket assembly.

DETAILED DESCRIPTION OF THE INVENTION

The following illustrations are examples of the invention described herein. It is contemplated that combinations of aspects of specific embodiments or combinations of the specific embodiments themselves are within the scope of this disclosure. While the methods, devices, and systems described herein are discussed as being used in conjunction with a gastric balloon device, the devices, methods, and systems of the present disclosure can be can be used with other fluid-filled devices or systems where automatic release of the fluid in the device or system might be required or beneficial or where automatic release of the fluid between any two separated spaces in which unassisted (that is, without direct human manipulation or intervention) opening of a fluid passage between the two spaces is desired.

Figure 1:
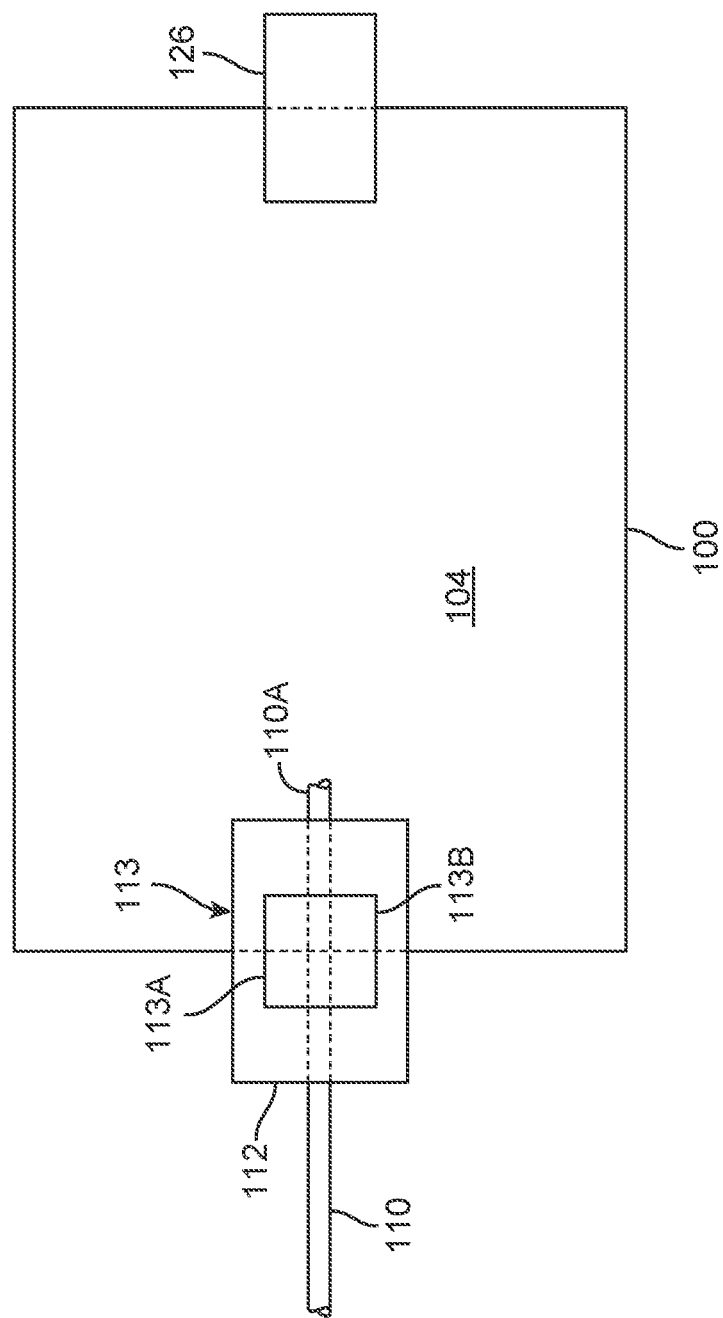
FIG. 1 is a block diagram of a fluid fillable balloon device.
Figure 2:
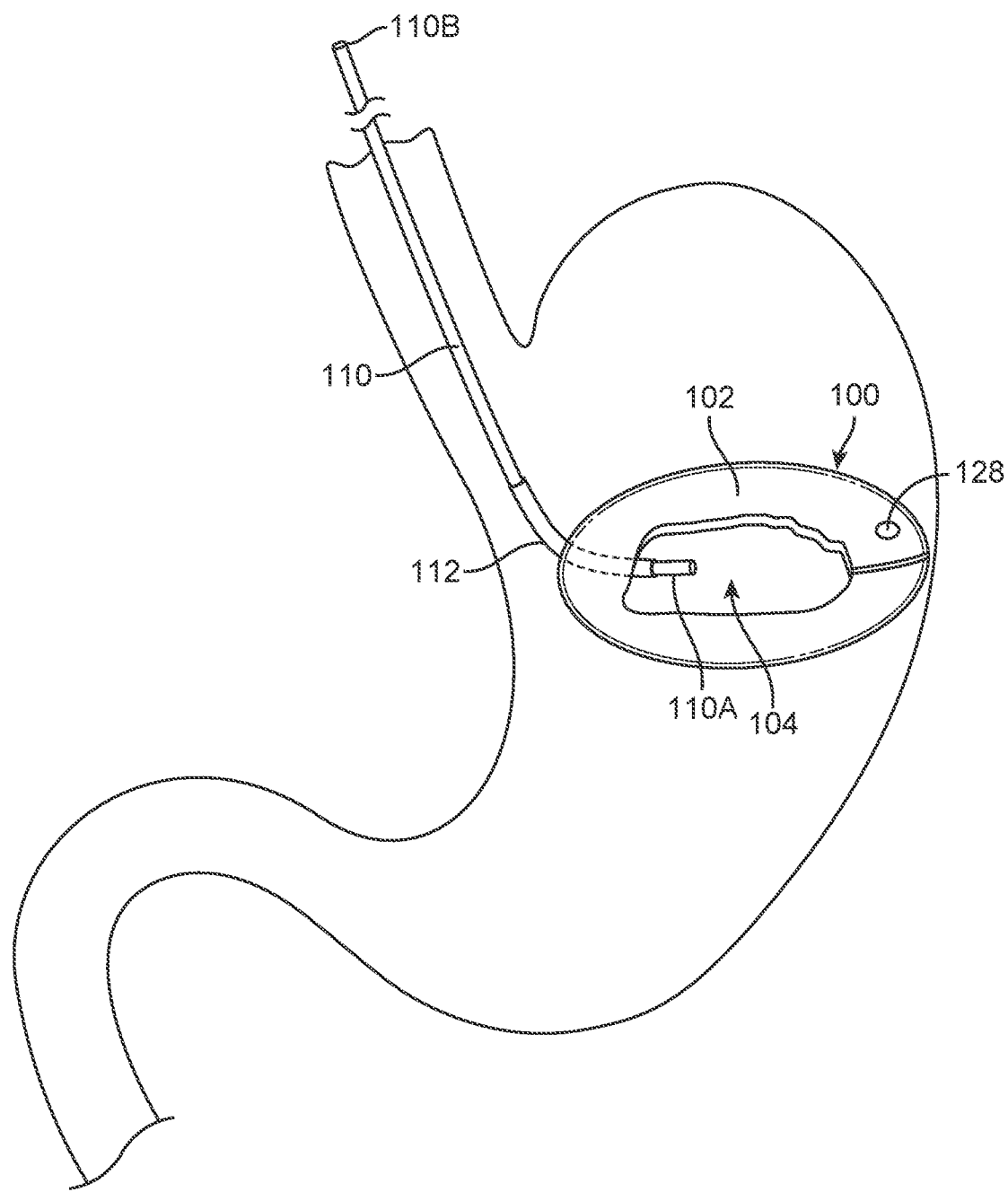
FIG. 2 illustrates a gastric balloon in situ after filling.

FIG. 1 illustrates schematic block diagram of an exemplary fluid fillable balloon device; in particular, it illustrates a gastric balloon device assembly 100. FIG. 2 is an illustration of device 100 in place in a patient's stomach after it has been inflated but before the filling tube has been removed. The device generally comprises two states of interest: a pre-deployment or uninflated configuration and a deployed, inflated or active configuration; the deployed configuration is shown. Generally, the device is inflated with a fluid delivered through a tube 110, also referred to herein as a catheter or conduit, wherein the tube may pass through a lumen in the wall of the balloon device or is coupled to a fluid path 112 between the exterior and the interior of the balloon device. In certain balloon devices the wall 102 of the balloon is fabricated from a thin film material such as, for example, polyurethane. In some variations the tube comprises a balloon end or internal section 110A that extends through fluid path 112 into the central enclosed space or reservoir 104 of device 100. In other variations internal section 110A stops short of the reservoir 104. The conduit 110 can be removed from the device once inflation is completed or after partial inflation. When the conduit is removed, fluid path 112 must be sealed to prevent the inflation fluid from leaking out, where sealing is accomplished by fill valve 113, illustrated in FIG. 1, which may comprise an external section 113B, an internal section 113A. In some variations, elements of the fill valve 113 have components installed inside conduit 110 as well as in fluid path 112. Other variations of the balloon device may be self-inflating, wherein, for example, two reactive chemicals pre-stored inside the uninflated balloon combine once the balloon is in place. The combined materials, such as an acid and bicarbonate of soda, give off a gas that inflates the balloon.

Figure 3A:
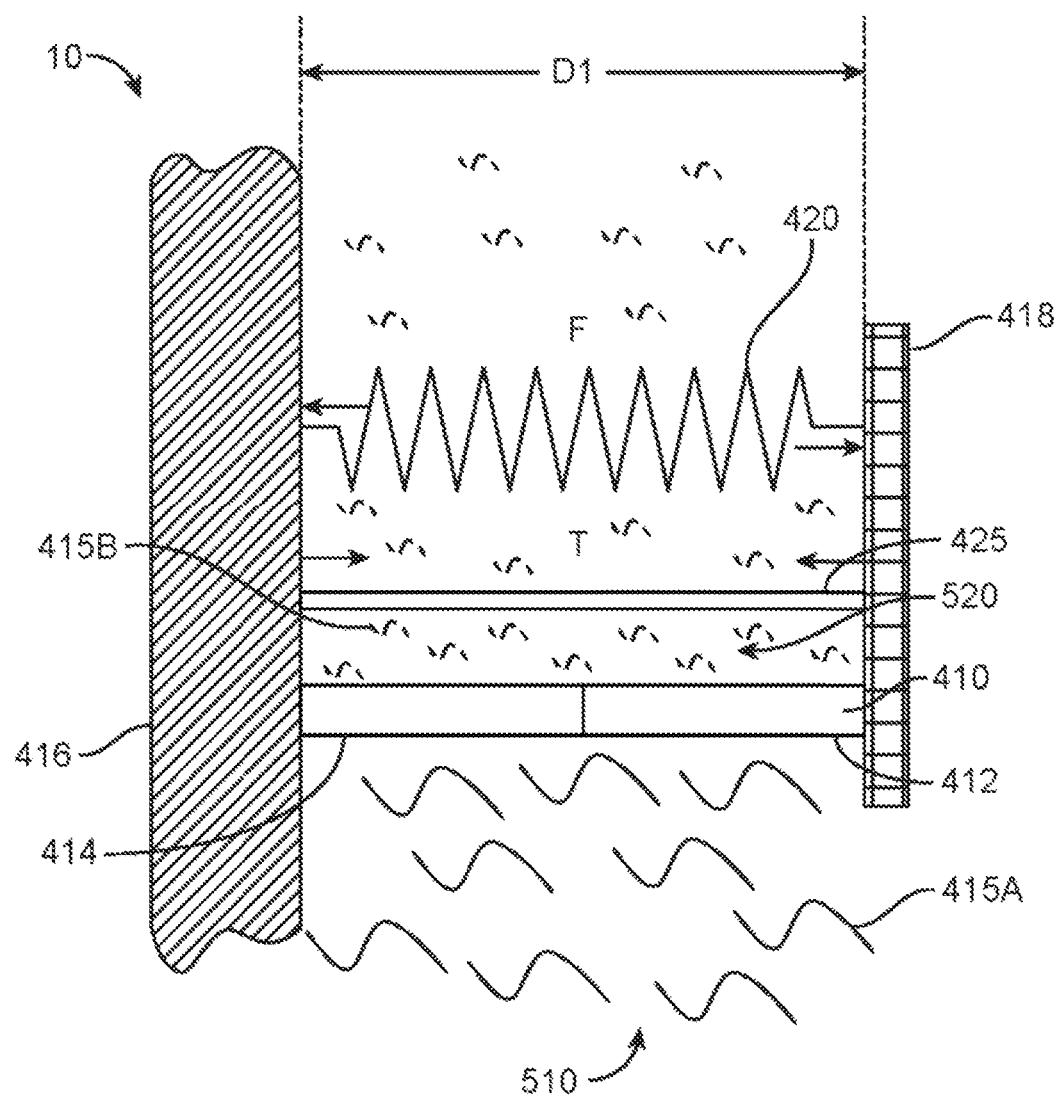
FIG. 3A is a mechanical schematic showing the functional elements of a fluid control valve system, shown in its normally closed state.

It is typically the case that release valve 126 is a single-use device; that is, once it opens to release fluid it cannot close, or at least is not closed, again. In some variations, as illustrated in FIG. 2, the valve may comprise a patch 128 of degradable material, which degrades or opens when exposed to either the natural stomach fluids or the filling fluid contained within reservoir 104. Once patch 128 degrades, the filling fluid is free to escape into the patient's stomach. In certain cases, the degradation rate of the patch, and the resulting flow rate, cannot be controlled adequately. The release valves described herein improve the timing and adequacy of the flow rate of the release of filler fluids by controlling the degrading fluid and by providing a FIG. 3A is an exemplary mechanical schematic diagram of a fluid control valve system 10 that has a binary flow condition or operation, where "binary" indicates that the valve comprises an open state and a closed state. Where in the closed state the valve is closed to either fully or significantly prevent fluid flow. In the open state, the valve allows partial or maximum fluid flow. It will be understood that a mechanical schematic diagram is a simplified representation of the functional components of a mechanical system and the mechanical relationship therebetween. It does not necessarily represent the physical forms of the mechanical elements nor the physical layout, attachment, or configuration of any actual components.

Returning to FIG. 3A, the binary operation of control valve system 10 is achieved through the addition of an energy storage device disposed to force the valve to the fully open condition, a valve system 10 is disposed between two otherwise isolated spaces, spaces 510 and 520, at least one of which contains a fluid 415A. In some variations the second space also contains a fluid 415B. In this variation, a valve system 10 includes three core mechanical components. The main component is a valve mechanism 410 that blocks or unblocks the flow of fluid from one space to the other. Schematically in FIG. 3A valve mechanism 410 is depicted as comprising a two element gate (412, 414), where one element of the gate is a base 414 and a second element is a traveler 412 where traveler 412 and base 414 abut tightly enough to block the flow of any fluid 415A/415B through valve mechanism 410. Note again that a mechanical schematic only represents functional elements and is not intended to indicate the physical form of the element effecting that function.

As further illustrated, valve system 10 comprises a second core component, an energy storage device 420, for example a spring, where the energy storage device is disposed to move traveler 412 away from base 414. In the schematic a base support 416 and a head 418 have been included to schematically illustrate a connection between energy storage device 420 and valve mechanism 410. In the normal operation of valve system 10, energy storage device 420 is initially in a high energy storage configuration and disposed between head 418 and base support 416 with a distance D1 between head 418 and base support 416. The compressed energy storage device 420 generates a force F directed to push traveler 412 away from base 414, as indicated by the arrowheads at the ends of spring 420. Energy storage device 420 does not need to be attached to either head 418 or base support 416 (or, equivalently base 414 or traveler 412). Alternatively, one or both sides of the device can be connected to the respective adjacent head 418 or base support 416.

The third core component of a valve system 10 is a restraining element 425. Under normal initial operation of valve system 10, restraining element 425 is also disposed between head 418 and base support 416, where restraining element 425 is in tension T which holds head 418 and base support 416 from moving apart, as indicated by the arrowheads showing the forces felt by head 418 and base support 416.

Figure 3B:
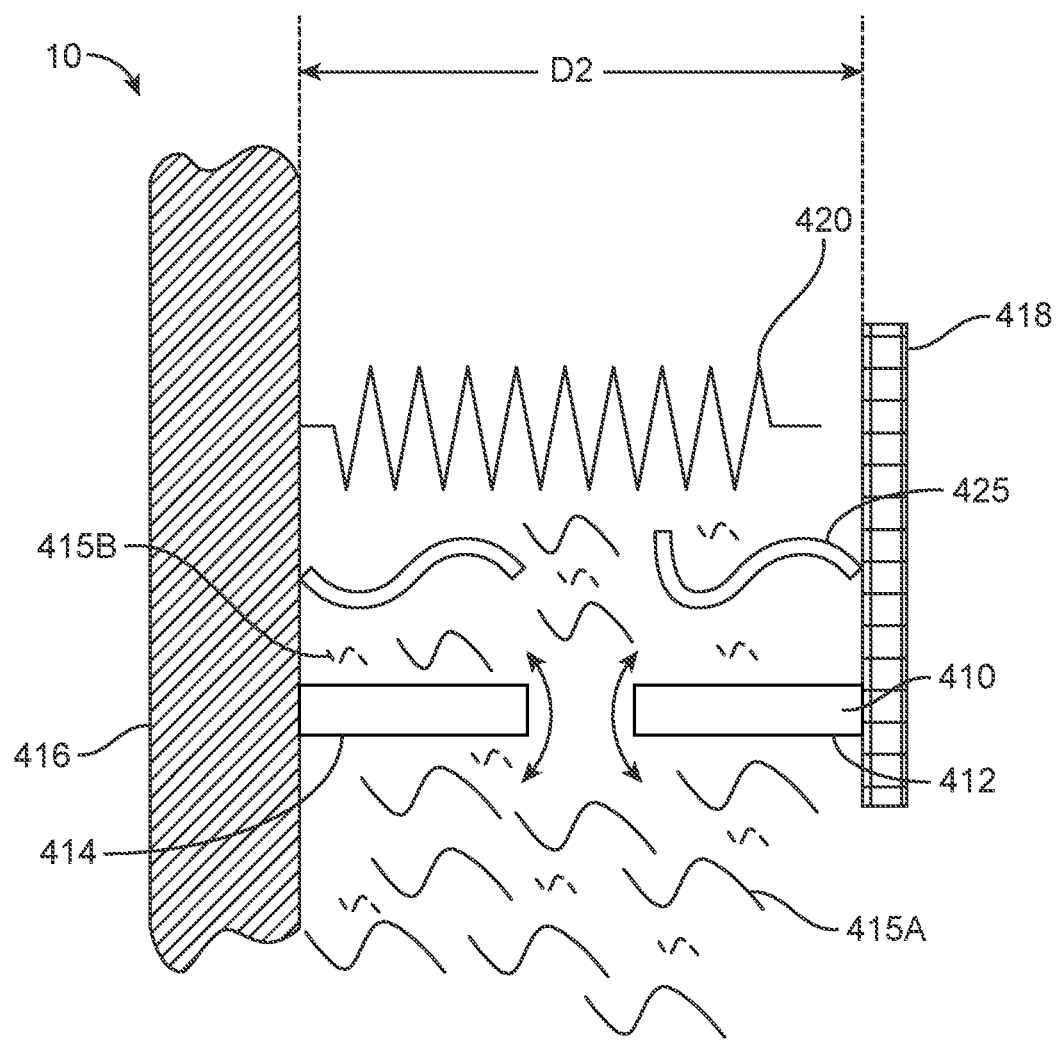
FIG. 3B is a mechanical schematic showing the fluid control valve system of FIG. 4A in its opened state after the stored energy has been released.

Valve system 10 switches between the no-flow condition, shown schematically in FIG. 3A, and the full-flow condition, shown schematically in FIG. 3B, when restraining element 425 loses its ability to counteract the force F of energy storage device 420. Depending on the designer's needs, restraining element 425 can be designed to lose strength by changing its temperature, by hydrolysis, by dissolution, by oxidation, or by any means appropriate for the restraining material and operational environment. Typically restraining element 425 breaks when the spring force exceeds the remaining strength of element 425, as illustrated in the figure, but element 425 may also lose its ability to maintain the required tension if it plasticly deforms, that is, stretches permanently, or elastically deforms.

As shown in FIG. 3B, the failure of restraining element 425 allows energy storage device 420 to increase the distance between base support 416 and head 418 to D2, thereby allowing fluid flow through valve mechanism 410 as shown by the arrows. In FIG. 3B, head 418, traveler 412, and a portion of restraining element 425 no longer have a connection to base support 416 indicating that those parts of fluid control valve system 10 are free to float away by a distance greater than D2. In other variations energy storage device 420 may be attached to head 418 instead of base support 416 while in yet other variations energy storage device 420 may connect head 418 and base support 416 even after opening, in which case D2 is the length of energy storage device 420 in its low energy condition (e.g., no longer in compression). In yet other variations energy storage device 420 is not physically attached to either base support 416 or head 418, in which case it may become a free-floating element once the constraining tension of restraining element 425 is removed.

Figure 3C:
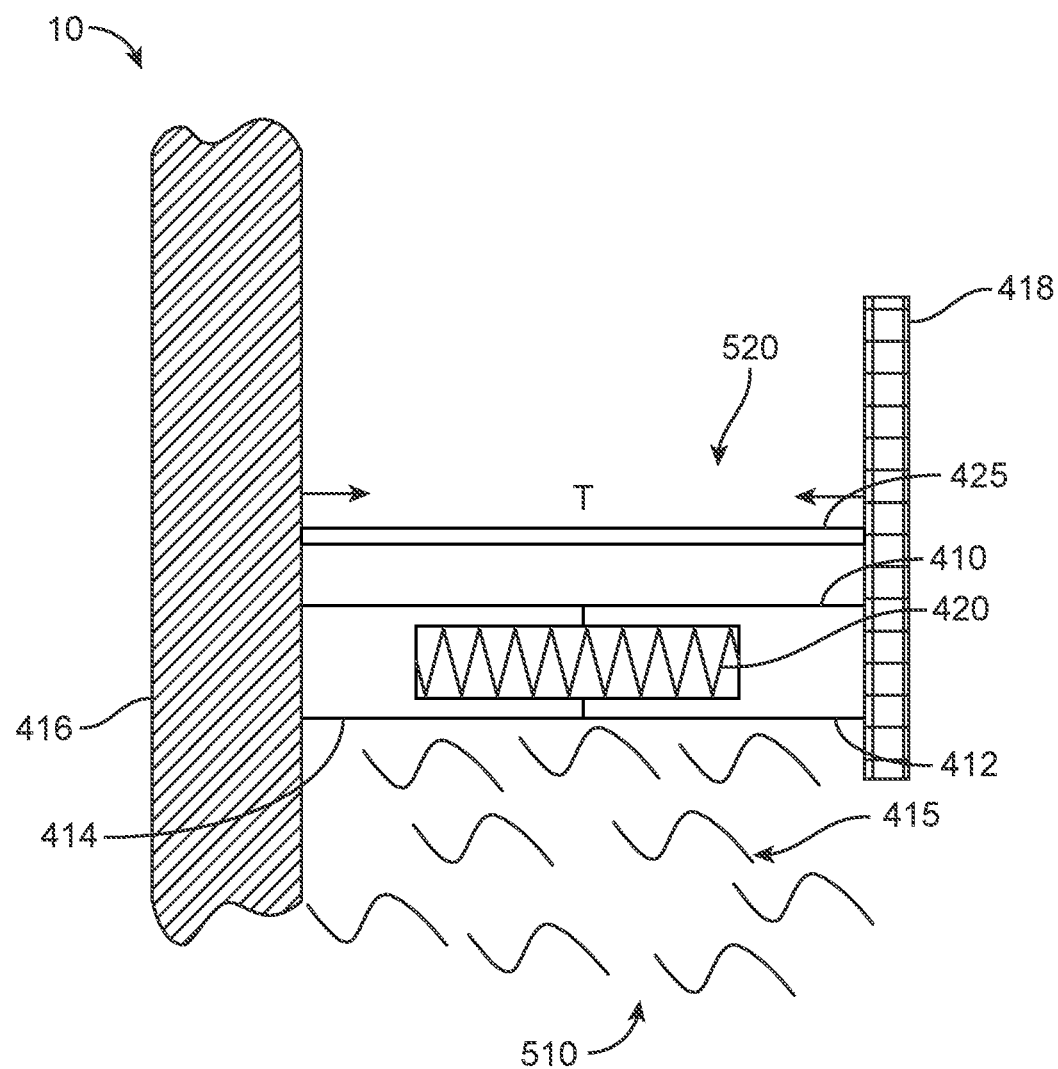
FIGS. 3C-3G are alternative mechanical schematics of the fluid control valve system
Figure 3D:
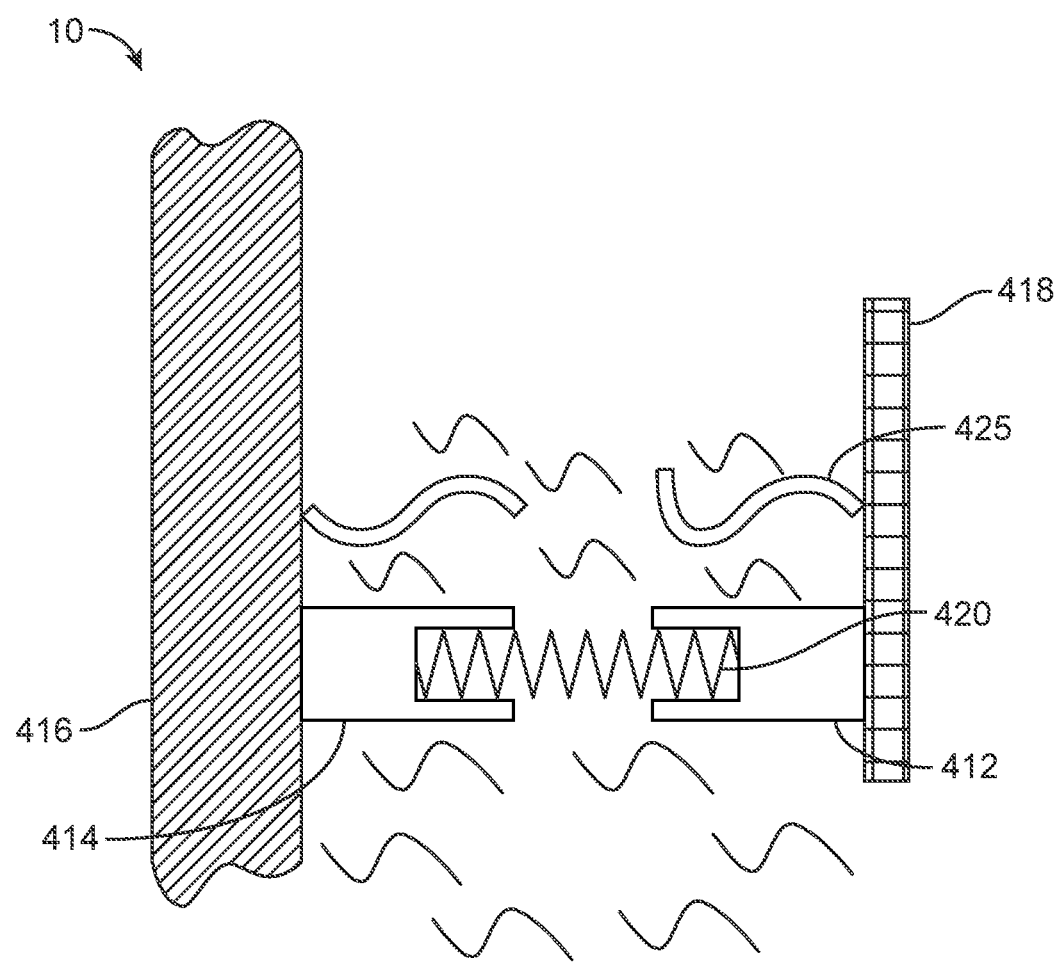
Figure 3E:
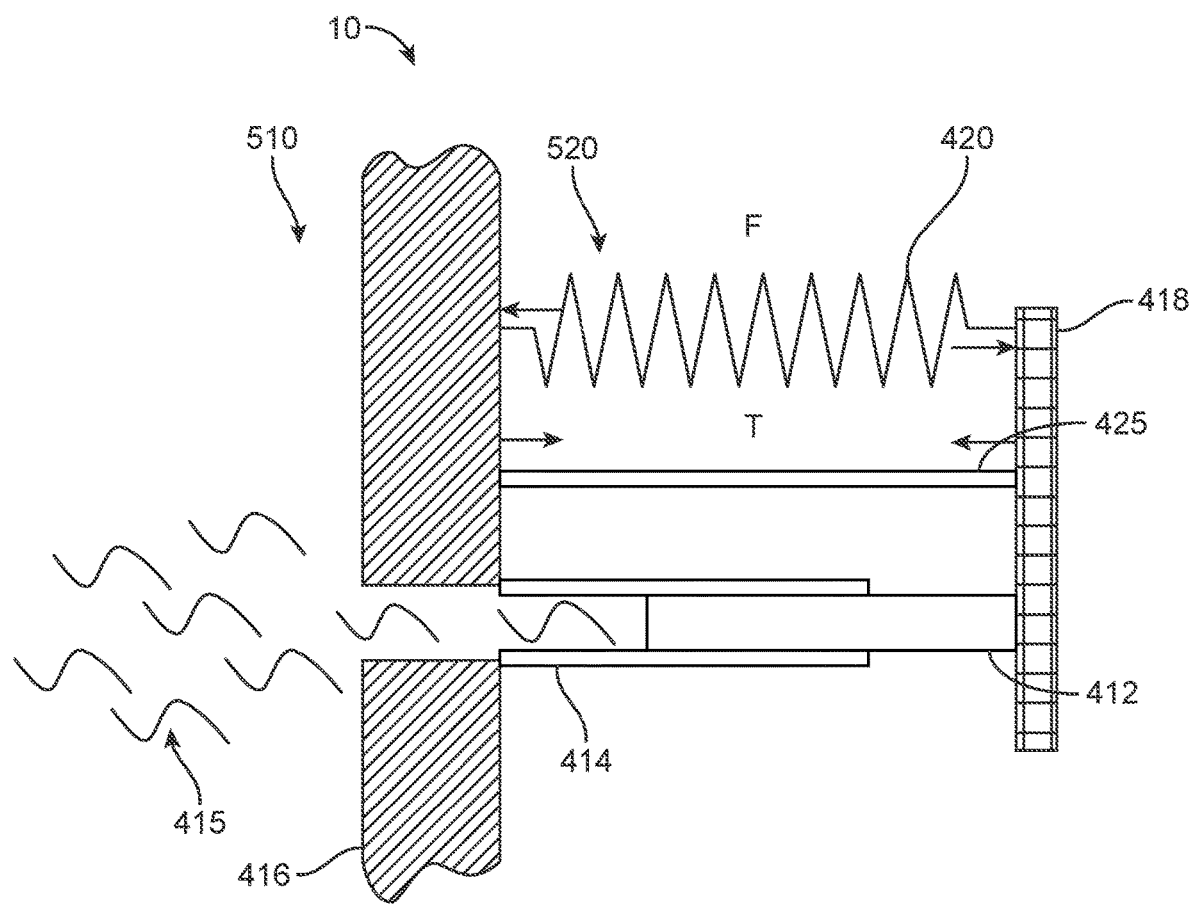
Figure 3F:
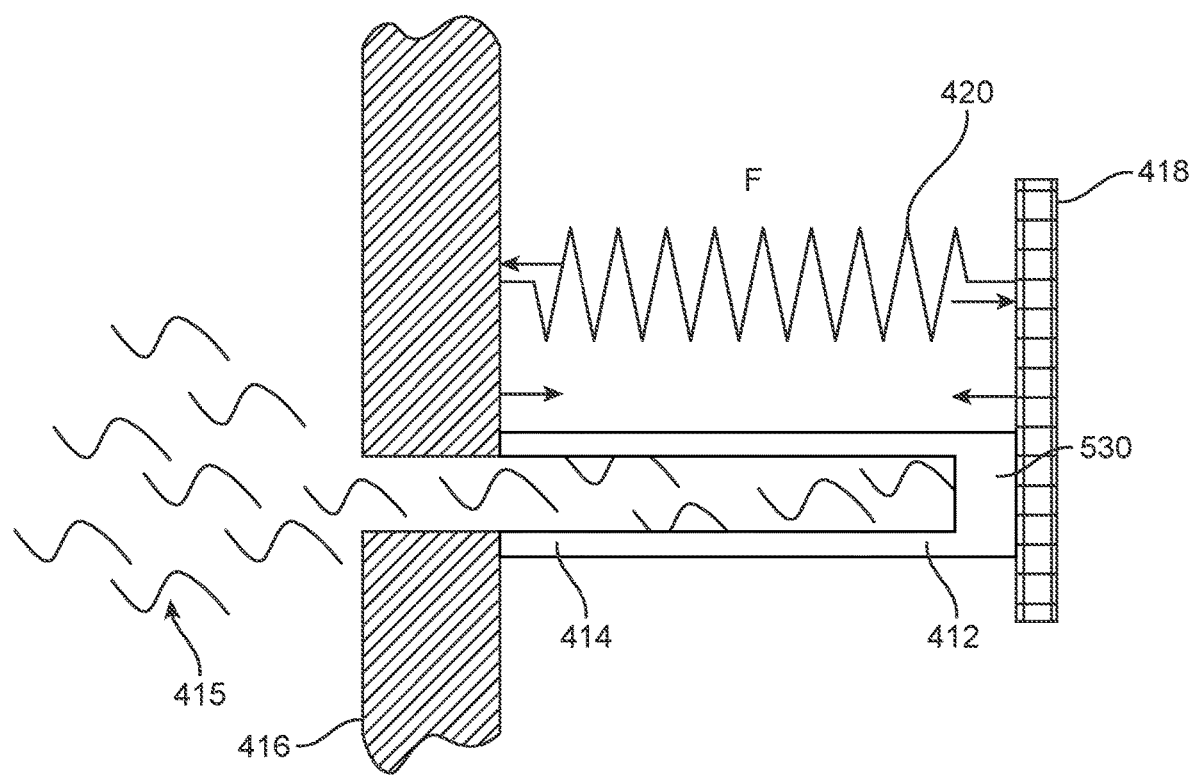

As was noted above, mechanical schematic diagrams are not intended to suggest or describe actual embodiments of the mechanical system; they only explain the mechanical functional relationships in the mechanical system. For example, FIGS. 3C, 3E, and 3F are alternative mechanical schematics of the same fluid control valve system as depicted in FIG. 3A. FIG. 3C illustrate a variation in which base 414 and traveler 412 sandwich energy storage device 420 between themselves directly (that is, the spring sits between the two portions and directly bears on them to move them apart) while restraining element 425 is directly or indirectly attached to the exterior of the "sandwich" to hold base 414 and traveler 412 tightly together, compressing energy storage device 420. The mechanical schematic of FIG. 3D illustrates the after-release mechanical relationships of the elements in the schematic of FIG. 3C.

FIG. 3E illustrates schematically a variation of the valve system in which base 414 is in the form of a fluid path 450 which channels fluid 415 between the isolated spaces 510, 520. Traveler 412 forms a plug or stopper that blocks fluid path 450 when the valve system is in its normally closed condition. Drawn in this fashion, the mechanical schematic of FIG. 3E helps clarify the use of a control valve system 10 in fluid filled balloon applications an embodiment of which is discussed below.

In some variations of control valve system 10 it is possible to combine two or more functions into one physical element. As shown schematically in FIGS. 3F and 3G, in this variation the base, traveler, and restraining element are all embodied in a single close-ended tube 530. Initially, tube 530 is a sealed fluid path between spaces 510 and 520.

Figure 3G:
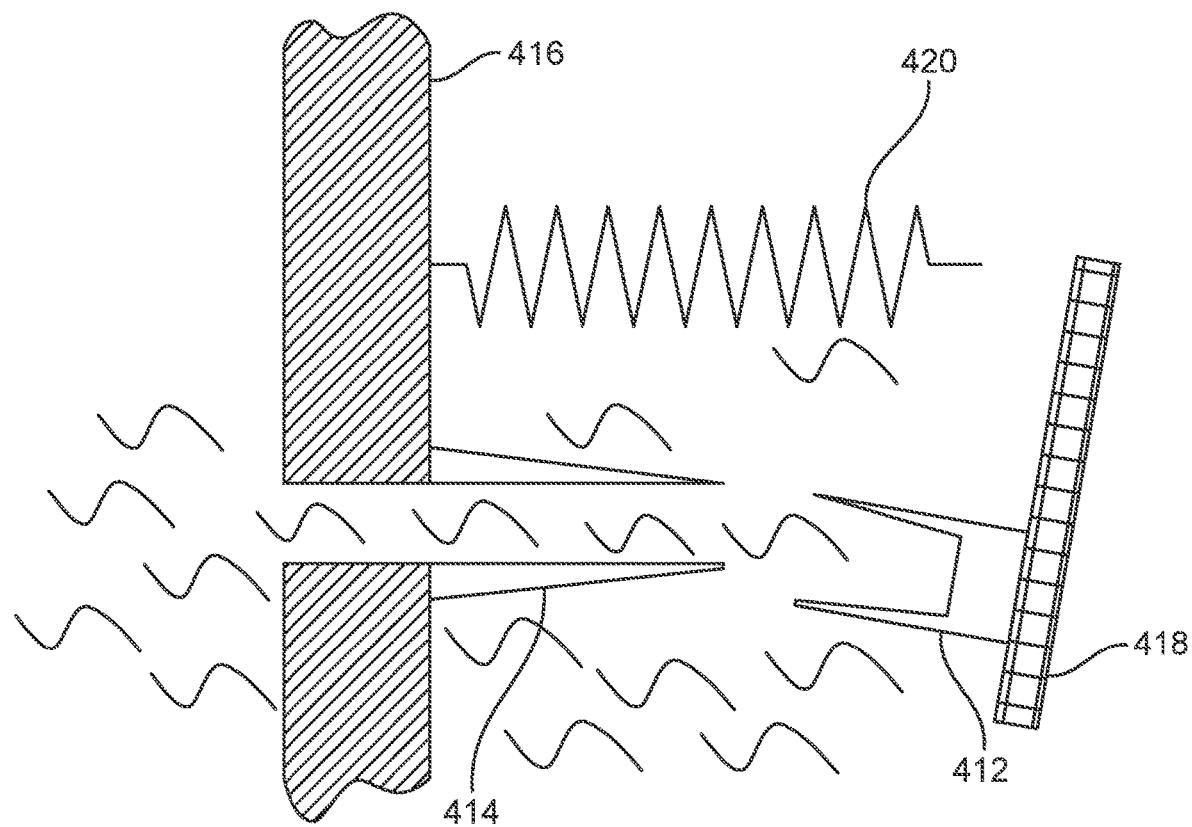

Energy storage device 420 is disposed to apply a force that is directed to pull the two ends 412, 414 of tube 530 apart. The two ends do not move apart while the walls of tube 530 remain strong enough to withstand the applied force. When the restraining element loses strength, as it is designed to do in specific environments, it will eventually allow the spring to pull tube 530 into two pieces, forming traveler 412 and base 414 and essentially allowing flow through the base support 416, as shown in FIG. 3G.

In yet another variation of valve system 10, not illustrated, base 414 and traveler 412 may comprise two jaws of a hinged component, with energy storage device 420 acting to open the hinge and restraining element 425 holding the hinge closed until element 424 loses strength as designed.

Other variations, also not illustrated, include energy storage devices in which the energy is stored by holding the device in an expanded, rather than compressed state.

Exterior Energy Storage Device

Figure 4:
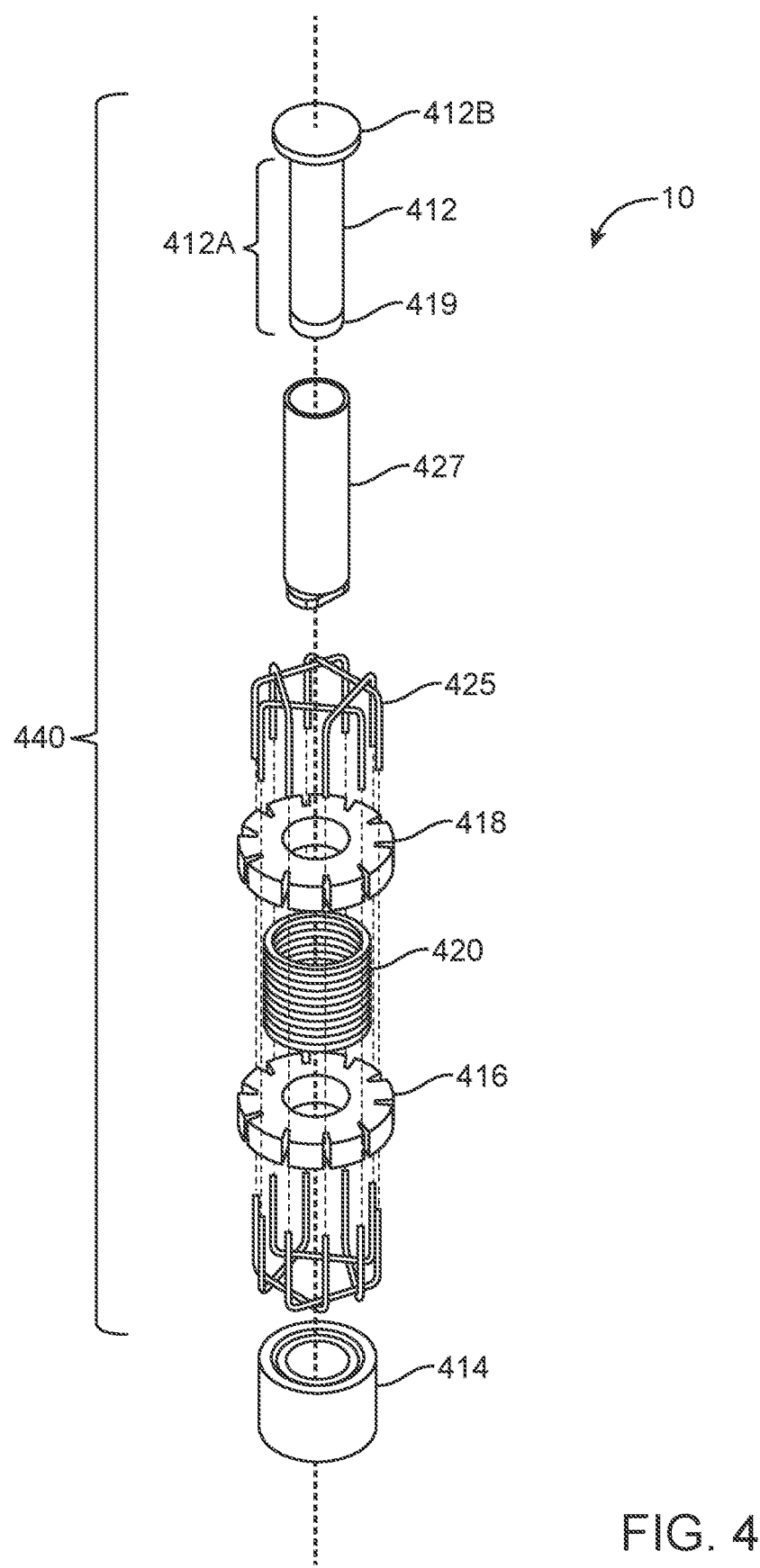
FIG. 4 is an exploded perspective view of a variation of a fluid control valve with an external energy storage device.

FIG. 4 is an exploded view of one variation of valve system 10 with an exterior energy storage device 420 in the form of a coil spring, where exterior indicates the spring 420 is exterior to the flow path through the valve system 10. In this variation, valve 410 of FIG. 3A comprises traveler 412 in the form of a plug or pin, base 414 in the form of a socket into which plug 412 is inserted, and a compliant gasket 427 that surrounds plug 412 to ensure a snug and leak-proof fit when plug 412 is inserted into socket 414.

Figure 5A:
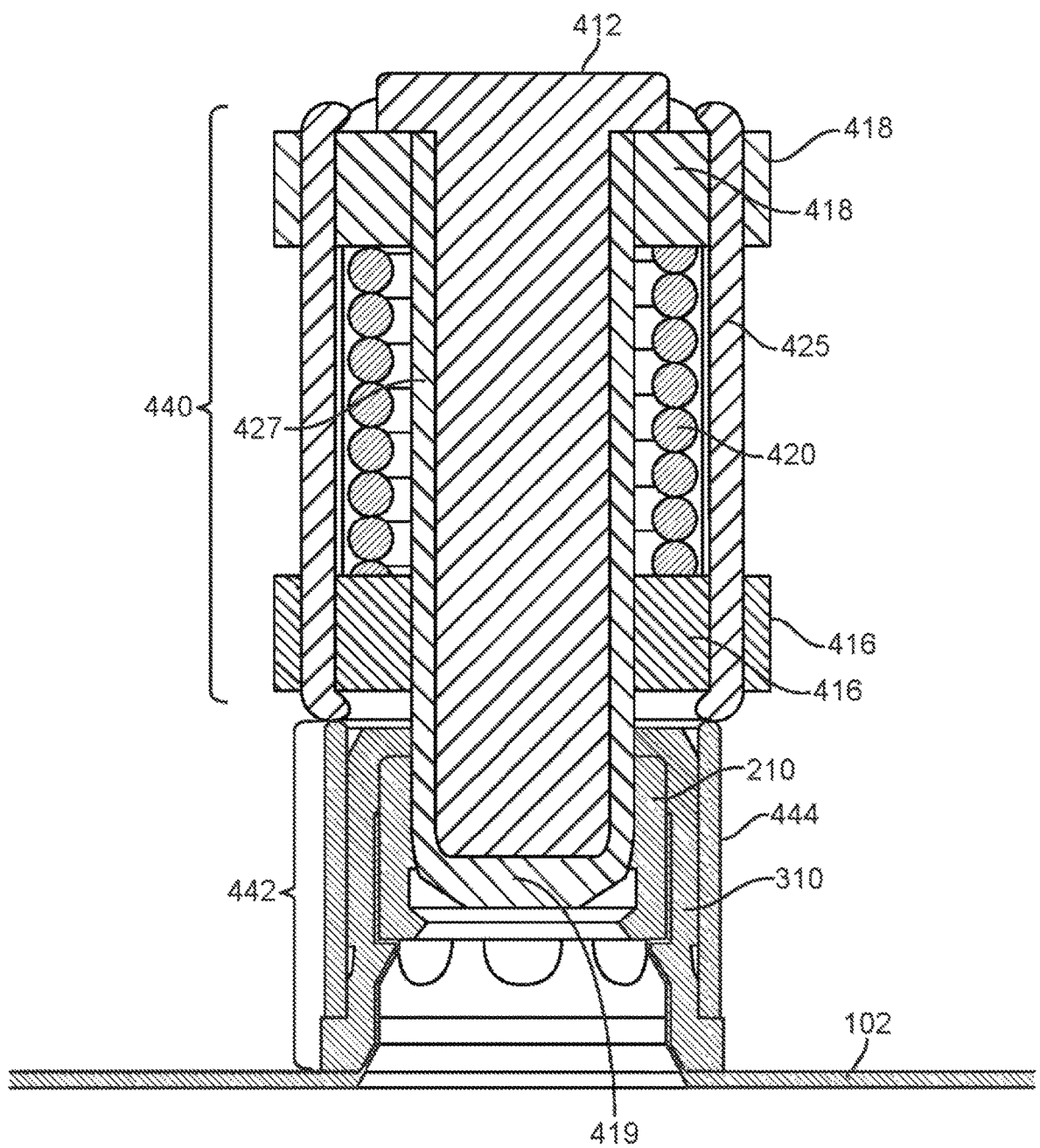
FIG. 5A is a sectional view of the fluid control valve of FIG. 4 as installed in a wall of thin film material.

As further illustrated in FIG. 4 and sectional view FIG. 5A, this variation of valve system 10 also comprises energy storage device 420 implemented as a coil spring disposed between a spoked head 418 and a substantially identical spoked base support 416, wherein restraining element 425 is a suture-like release material that is looped or stitched between the spokes of head 418 and base support 416. Head 418 and base support 416 each have a central hole large enough to accommodate plug 412 surrounded by gasket 427. In this variation release material 425 is stitched in a pattern to minimize tilting of head 418 relative to base support 416 both before and after initial release material breakdown.

As shown in the figures, in this variation plug 412 comprises an extended body 412A with a larger diameter pinhead 412B at one end, where the length of the extended body is designed to be longer than the length of the compressed coil spring 420 plus the thicknesses of the head 418 and base support 416, and the diameter of pinhead 412B is designed to be larger than the hole in head 418 to prevent plug 412 from fully entering or passing through the hole in head 418. The spring, head, base support, and release material comprise a valve release subassembly 440.

In this variation socket 414 is essentially a cylindrical tube disposed between the two spaces comprising a central lumen that allows fluid flow between the two spaces. In many variations socket 414 is fabricated as a socket subassembly 442 that allows the socket to be attached to the wall 102 separating the two spaces, as will be described below.

This variation of valve system 10 is assembled by inserting plug 412 (with gasket 427), through the lumen in valve release subassembly 440 formed by the open central region of coiled spring 420 such that a tip 419 of plug 412 extends beyond the end of valve release subassembly 440 by a designed length. As further illustrated in FIGS. 4 and 5A, the exposed tip 419 of plug 412, surrounded by gasket 427, is subsequently inserted into socket subassembly 442, where the gasketed tip 419 seals the lumen in socket subassembly 442 against fluid flow. In some variations tip 419 of plug 412 is bulbous to compress gasket 427 against the innermost surface of socket assembly 442 while providing a leading edge that guides tip 419 into the lumen.

As shown in FIG. 5A and in perspective view in FIG. 6, valve system 10 can be installed to control fluid flow between two spaces separated by a wall 102 of thin film material. While FIGS. 1 and 2 suggest the use of a valve system 10 to release fluid from a gastric balloon fabricated from thin film material, this is but an exemplary use. The valves described herein may be used in any situation where there is a fluid impervious barrier material separating two spaces and where fluid may be present on either or both sides of the barrier material. For example, a valve system 10 can be used to temporarily separate two reactive chemicals where one chemical is in fluid form.

Figure 5B:
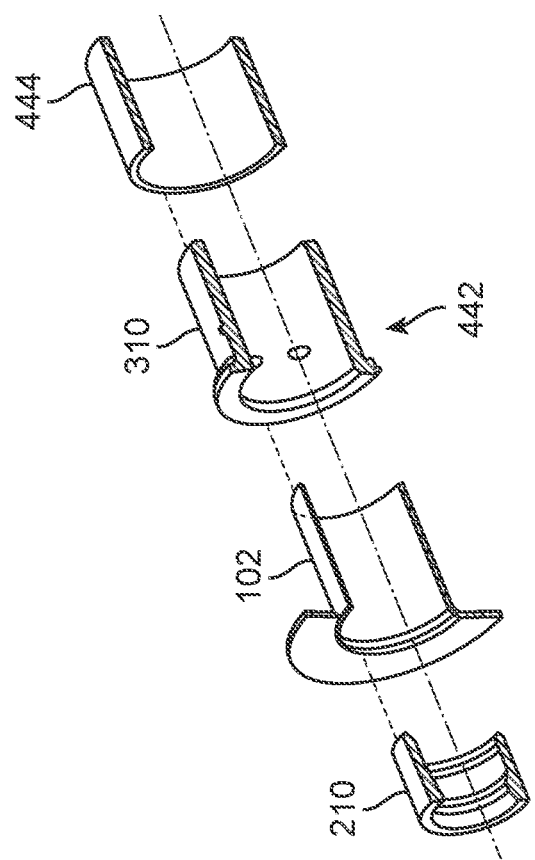
FIG. 5B is an exploded view of one variation of a socket assembly.

As illustrated in FIG. 5B, socket subassembly 442 is attached to wall 102, through which a hole is provided for fluid flow. There are several ways to attach socket subassembly 442 to a wall, for example gluing or welding, where the preferred method of attachment is an engineering decision based, among other considerations, the material properties of wall 102 and socket assembly 442. In the illustrated variation, where wall 102 is a thin polymeric sheet, mechanically attaching socket assembly 442 is used for example. In this variation socket assembly 442 comprises three parts: a retaining ring 444, a wall anchor 310, and a gasket jacket 210.

Gasket jacket 210 is a thin-walled, hollow cylinder. The inner wall of the hollow cylinder is sized, and sometimes shaped, to grip the compliant, gasketed tip 419 of plug 412. For example, the inner wall may be tapered to have a wider opening to accept plug 412 and to guide the tip 419 into a narrower portion wherein the compliant gasket is squeezed to make a tight fit. The inner wall may be inscribed with a number of circumferential ridges and grooves to better grip the compliant gasket. Or for example, in some variations, the inner wall may have an indented groove with a circular segment cross-section that matches the bulbous tip 419 of the gasketed plug; this groove acts a detent to provide a positive hold on tip 419.

Wall anchor 310 is the primary means to attached gasket jacket 210 to a thin-film wall 102. It is used to pinch a shaped section of wall 102 against the exterior of gasket jacket 210. This pinching behavior is illustrated in the exploded, cross sectional view of socket assembly 442 of FIG. 5B. The wall section starts out as a flat sheet but takes on the illustrated "stovepipe hat" shape after being stretched over a mandrel. Gasket jacket 210 is then inserted inside the wall section, most easily from the "brim" side of the stovepipe hat while wall anchor 310 is slipped over the exterior of the "pipe" section of the stovepipe, thereby trapping the wall material between jacket 210 and anchor 310. In many variations anchor 310 is fabricated from a soft material, for example a plastic, and toleranced to enclose the wall material without pulling or tearing it. Finally, a retaining ring 444 is placed over anchor 310 to squeeze it tightly against wall material 102, pinching the material against gasket jacket 210.

FIG. 6 illustrates one method for inserting plug 412 (with valve release subassembly 440 in place) into a socket assembly 442 that has been pre-installed in a wall 102. As shown, gasket 427 is extended by a convenient length to form a gasket extension 427A that extends a convenience distance beyond plug tip 419. This extended length 427A is not filled by any solid and can easily be threaded through the lumen in gasket jacket 210. A portion 427B of gasket extension 427A emerges through the lumen in gasket jacket 210 on the opposite side of wall 102 from plug 412. Gasket extension 427A moves with relative ease through gasket jacket 210 because there is no plug inside this portion of the gasket. Tip 419 of plug 412 is drawn into gasket jacket 210 by pulling on gasket extension 427B until tip 419 is captured by jacket 210. By design, tip 419 and the gasket around it cannot pass fully through the lumen, so continuing to pull on gasket extension 427B creates an increasing tension on gasket 427.

When the elastic limit of gasket 427 is reached, the gasket tears into two sections. In some variations a preferential detachment point 429 is created in gasket 427 by weakening the gasket at a pre-determined location by partially cutting through the gasket, creating a circumferential score, or otherwise weakening the gasket at the desired location. Typically, the desired location separates gasket 427 from gasket extension 427A. Using a preferential detachment point created by weakening the gasket allows the designer to control how much force is required to tear the gasket, where the tear will be, and ensure a clean tear between the removed portion of the gasket and the gasket surrounding tip 419 to seal the valve.

For the illustrated variation, the valve is installed in a fluid impervious wall 102 separating two spaces on either side of the wall, where at least one space has a fluid. Plug 412 substantially fills the lumen in gasket jacket 210 and presses gasket 427 against the inner wall of the lumen in gasket jacket 210 to seal the lumen against fluid transfer. For convenience, the space in which release valve subassembly 440 is located will be designated as first or interior space and is bounded by wall 102. By design, release material 425 is susceptible to deterioration when exposed to the environmental conditions in the interior space. In many variations the release material is filamentary. Examples of release materials that are available in filamentary suture form can include Polyglycolide (PGA), Polydioxanone (PDS), Poly (lactic-co-glycolic acid) (PLGA), Polylactide (PLA), Poly (4-hydroxybutyric acid) (P4HB), Polyglactin 910, and Polycaprolactone (PCL). In some variations the interior space may be filled with a fluid which, over a designed period of time, dissolves or hydrolyses the suture. In other variations, for example, release material 425 may be melted or softened by increasing the temperature in the interior space.

Independent of the way release material 425 is weakened, after a designed time period the residual strength of release material 425 is inadequate to constrain the stored energy in spring 420. As spring 420 expands it causes head 418 and base support 416 to separate. By definition, as they separate the distance between them enlarges. Prior to release material deterioration, extended body 412A reached between the top of head 418, through base support 416, and into socket 414. As the distance between head 418 and base support 416 increases, extended body 412A is pulled into valve release subassembly 440 from the base support end, plug 412 being prevented from entering head 418 by pinhead 412B. As extended body 412A is pulled into valve release subassembly 440 it is automatically extracted from socket 414, opening fluid control valve system 10 to allow fluid transfer between the interior space and a second or exterior space exterior to the wall 102.

What is claimed:

1. A fluid control valve for controlling fluid flow, the fluid control valve comprising:
   a base defining a fluid path therethrough such that the fluid path is fluidly coupled between a first space and a second space;
   a traveler structure moveable relative to the base between an open configuration and a closed configuration, where in the open configuration the traveler structure permits fluid flow through the fluid path between the first space and the second space, and where in the closed configuration the traveler structure prevents flow through the fluid path;
   an energy storage device disposed between the traveler structure and the base;
   a restraining element that restrains the energy storage device in a stored energy condition where the traveler structure is in the closed configuration, where the restraining element is configured to degrade such that degradation of the restraining element releases the energy storage device from the stored energy condition to cause the traveler structure to move to the open configuration relative to the base, wherein the restraining element is configured to reduce in a mechanical integrity over a pre-determined period during exposure to environmental conditions.

2. The fluid control valve of claim 1, wherein the restraining element is configured to degrade in response to temperature change, hydrolysis, dissolution, or oxidation.

3. The fluid control valve of claim 1, wherein the restraining element is configured to degrade in response to a fluid in fluid communication with the restraining element.

4. The fluid control valve of claim 1, where the restraining element is located in the first space and is isolated from the second space.

5. The fluid control valve of claim 1, where the restraining element is located in the second space and is isolated from the first space.

6. The fluid control valve of claim 1, where the restraining element is located outside of the fluid path.

7. The fluid control valve of claim 1, where the restraining element forms a portion of the fluid path.

8. The fluid control valve of claim 1, where the restraining element is located within the fluid path.

9. The fluid control valve of claim 1, where the traveler structure comprises a binary configuration when in the open configuration or in the closed configuration, such that the fluid control valve comprises a binary fluid control valve.

10. The fluid control valve of claim 1, wherein the traveler structure and the restraining element comprise a single part.

11. The fluid control valve of claim 1, where the traveler structure separates from the restraining element upon degrading to release the energy storage device from the stored energy condition.

12. A fluid control valve for controlling fluid transfer between a first space and a second space on either side of the fluid control valve, comprising:
   a plug receptacle installed in a wall separating the first space from the second space, the plug receptacle providing a lumen along a length of the receptacle that forms a fluid path between the first space and the second space, the lumen having a cross-sectional shape with internal, cross-sectional dimensions;
   a fluid plug having a capping end, an insertion end, and an extended body running therebetween, where the fluid plug has a cross-sectional shape and outer dimensions configured to form a fluid seal when the extended body and insertion end are inserted into the plug receptacle;
   a plug extraction head at the fluid plug capping end;
   a reaction force head disposed exterior to the plug receptacle and further disposed towards the insertion end relative to the plug extraction head;
   an energy storage device disposed between the plug extraction head and the reaction force head and further disposed to increase a separation between the plug extraction head and the reaction force head when in an unconstrained state;
   a release material attaching the plug extraction head to the reaction force head and causing the energy storage device to be in a constrained state;
   wherein a reduction in a mechanical integrity of release material causes the energy storage device to assume the unconstrained state, which applies a force to increase the separation between the plug extraction head and the reaction force head, and where motion of the reaction force head is at least initially constrained, directing the force towards the plug extraction head, whereby the fluid plug is extracted from the plug receptacle.

13. A fluid control valve for controlling fluid flow, the fluid control valve comprising:
   a base defining a fluid path therethrough such that the fluid path is fluidly coupled between a first space and a second space;
   a traveler structure moveable relative to the base between an open configuration and a closed configuration, where in the open configuration the traveler structure permits fluid flow through the fluid path between the first space and the second space, and where in the closed configuration the traveler prevents flow through the fluid path;
   an energy storage device disposed between the traveler structure and the base;
   a restraining element, located outside of the fluid path and that restrains the energy storage device in a stored energy condition where the traveler structure is in the closed configuration, where the restraining element is configured to degrade when in fluid communication with a fluid such that degradation of the restraining element releases the energy storage device from the stored energy condition to cause the traveler structure to move to the open configuration relative to the base.

14. The fluid control valve of claim 13, where the restraining element is located in the first space and is isolated from the second space.

15. The fluid control valve of claim 13, where the traveler structure comprises a binary configuration when in the open configuration or in the closed configuration, such that the fluid control valve comprises a binary fluid control valve.

16. A fluid control valve for controlling fluid flow, the fluid control valve comprising:
   a base defining a fluid path therethrough such that the fluid path is fluidly coupled between a first space and a second space;
   a traveler structure moveable relative to the base between an open configuration and a closed configuration, where in the open configuration the traveler structure permits fluid flow through the fluid path between the first space and the second space, and where in the closed configuration the traveler structure prevents flow through the fluid path;
   an energy storage device disposed between the traveler structure and the base;

a restraining element having a strength that restrains the energy storage device in a stored energy condition when the traveler structure is in the closed configuration, where the restraining element is configured to degrade to a reduced strength, wherein the restraining element is unable to restrain the energy storage device which causes the energy storage device to exert a force on the traveler structure to move the traveler structure relative to the base to the open configuration.

17. The fluid control valve of claim 16, wherein the restraining element is configured to degrade in response to temperature change, hydrolysis, dissolution, and oxidation.

18. The fluid control valve of claim 16, wherein the restraining element is configured to degrade in response to a fluid in fluid communication with the restraining element.

19. The fluid control valve of claim 16, where the restraining element is located in the first space and is isolated from the second space.

20. The fluid control valve of claim 16, where the restraining element is located outside of the fluid path.

21. The fluid control valve of claim 16, where the restraining element is located within the fluid path.

22. The fluid control valve of claim 16, where the traveler structure comprises a binary configuration when in the open configuration or in the closed configuration, such that the fluid control valve comprises a binary fluid control valve.

23. The fluid control valve of claim 16, wherein the traveler structure and restraining element comprise a single part.

24. The fluid control valve of claim 16, where the traveler structure separates from the restraining element upon degrading to release the energy storage device from the stored energy condition.

* * * * *

UNITED STATES PATENT AND TRADEMARK OFFICE
CERTIFICATE OF CORRECTION

| | | |
|---|---|---|
| PATENT NO. | : 11,098,813 B2 | Page 1 of 1 |
| APPLICATION NO. | : 16/505468 | |
| DATED | : August 24, 2021 | |
| INVENTOR(S) | : David W. Nelson | |

It is certified that error appears in the above-identified patent and that said Letters Patent is hereby corrected as shown below:

In the Specification

In Column 4, Line 16, please replace "controlling the degrading fluid and by providing a" with --controlling the degrading fluid.--

Signed and Sealed this
Fifth Day of December, 2023

Katherine Kelly Vidal
*Director of the United States Patent and Trademark Office*